Figure 1:
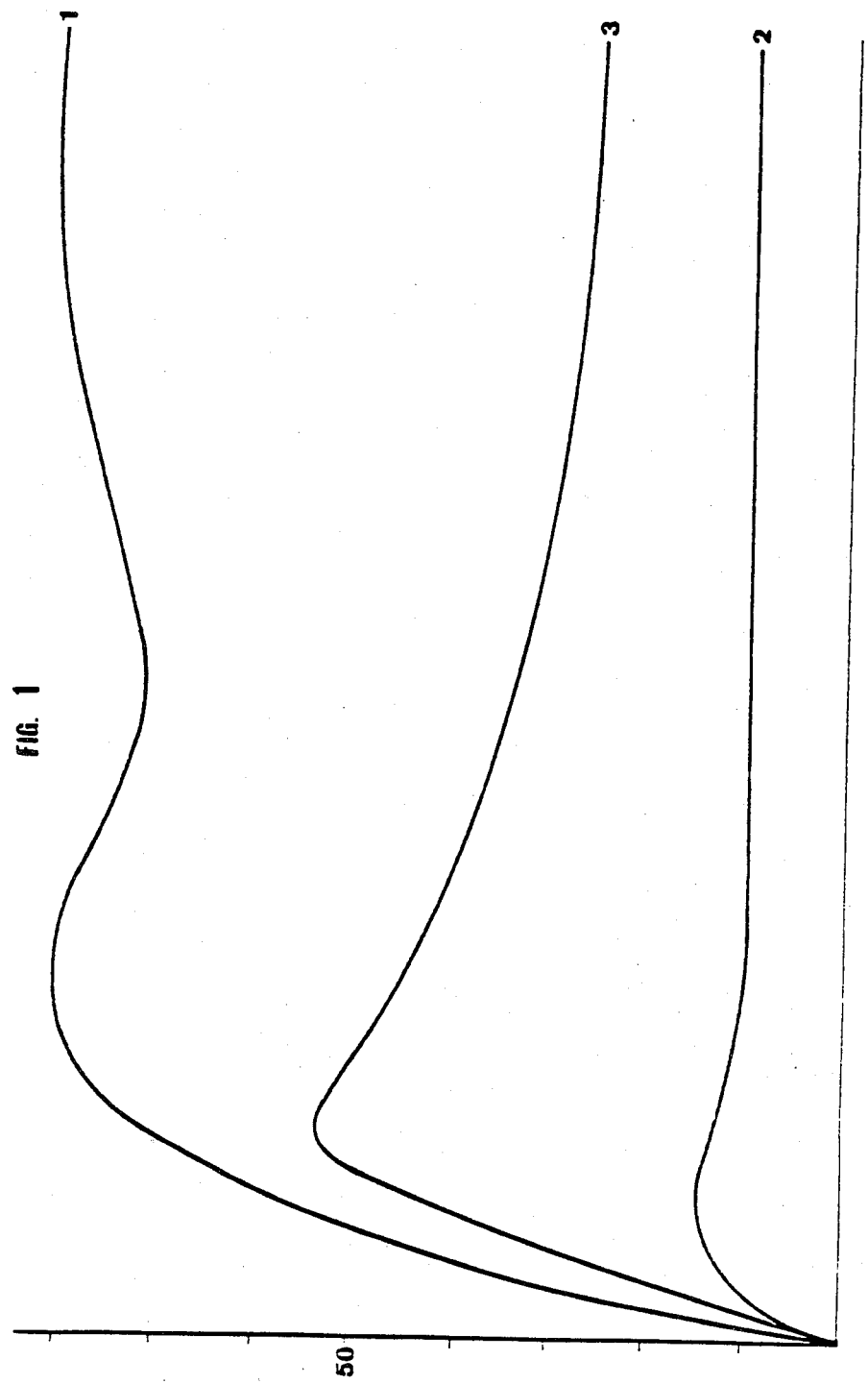

United States Patent [19]

Stramentinoli et al.

[11] 4,373,097

[45] Feb. 8, 1983

[54] PROCESS FOR PREPARING ADENOSINE DERIVATIVES OF ANTI-INFLAMMATORY AND ANALGESIC ACTIVITY

[75] Inventors: Giorgio Stramentinoli; Federico Gennari, both of Milan, Italy

[73] Assignee: BIORESEARCH S.r.l., Milan, Italy

[21] Appl. No.: 257,969

[22] Filed: Apr. 27, 1981

[51] Int. Cl.³ .............................................. C07H 19/16
[52] U.S. Cl. ...................................... 536/26; 536/24; 424/180
[58] Field of Search ..................... 424/180; 536/24, 26

[56] References Cited

U.S. PATENT DOCUMENTS 3,212,954  10/1965  Kuhn et al. .......................... 536/26

OTHER PUBLICATIONS

Chemical Abstracts, vol. 79, p. 402, Abst. No. 53743g, 1973.
Chemical Abstracts, vol. 77, p. 490, Abst. No. 114767a, 1972.

*Primary Examiner*—Blondel Hazel
*Attorney, Agent, or Firm*—Stevens, Davis, Miller & Mosher

[57] ABSTRACT

Therapeutic composition of antiinflammatory, analgesic and antipyretic activity comprising as its active principle at least one component of general formula:

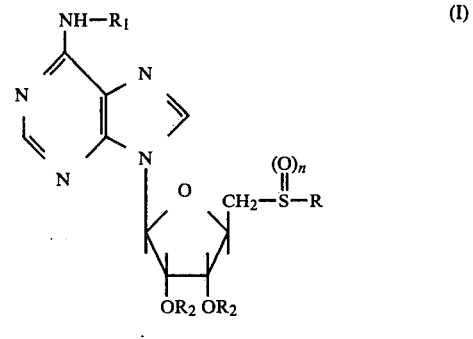

in which:

R is a linear or branched alkyl radical of 1–18 C atoms, or phenylalkylene in which the alkylene chain has 1–6 C atoms $R_1$ is H, an aliphatic acyl radical of 1–6 C atoms or an aromatic acyl radical $R_2$ is H, an aliphatic acyl radical of 1–6 C atoms, or an aromatic acyl radical, or alternatively the radicals $R_2$ together form an isopropylidene chain n is 0 or 1.

3 Claims, 4 Drawing Figures

PROCESS FOR PREPARING ADENOSINE DERIVATIVES OF ANTI-INFLAMMATORY AND ANALGESIC ACTIVITY

This invention relates to adenosine derivatives of anti-inflammatory, analgesic and antipyretic activity, and the therapeutic compositions which contain them as their active principle.

The compounds of therapeutic activity according to the present invention are of general formula:

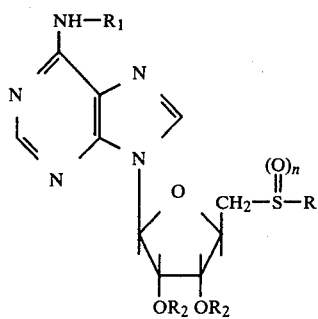

(I)

in which:

R is a linear or branched alkyl radical of 1-18 C atoms, of phenylalkylene in which the alkylene chain has 1-6 C atoms $R_1$ is H, an aliphatic acyl radical of 1-6 C atoms or an aromatic acyl radical $R_2$ is H, an aliphatic acyl radical of 1-6 C atoms or an aromatic acyl radical, or alternatively the radicals $R_2$ together form an isopropylidene chain.

n is 0 or 1.

Furthermore, when $R_1$ is H, the invention also relates to the acid addition salts of the compounds of formula (I).

Preferred meanings for R are: methyl, ethyl, propyl, isopropyl, butyl, isobutyl, sec.butyl, pentyl, hexyl, heptyl, octyl, decyl, dodecyl, hexadecyl, octadecyl or benzyl.

Preferred meansings for $R_1$ are: hydrogen, acetyl, propionyl, butyrryl, benzoyl or tosyl.

Preferred meanings for $R_2$ are: hydrogen, acetyl, propionyl, butyrryl, benzoyl or tosyl.

The preferred acid addition salts of the compounds of formula (I) are: chloride, sulphate, phosphate, formate, acetate, citrate, tartrate, methanesulphonate or p-toluenesulphonate.

The compounds of formula (I) are partly new.

The compounds of formula (I) are prepared by various methods according to the meaning of the various radicals.

For preparing the group of compounds of formula:

(Ia)

[structure shown]

in which R has the aforesaid meanings, the Legraverand method (Legraverand M. Ibanez S., et al. (1977) Eur. J. Med. Chem. 12, 105–108) has been followed, in which adenosine is converted into 5'-chloro-5'-deoxyadenosine by reaction with thionyl chloride in hexamethylphosphoramide.

The 5'-chloro-5'-deoxyadenosine is then converted into the required thioether by reaction with the corresponding mercaptan in a 2 N sodium hydroxide solution at 80° C.

The thioethers obtained are purified by recrystallisation from water or from lower aliphatic alcohols.

The compounds (Ia) can then be salified with the stoichiometric quantity of the required acid.

The compounds of general formula:

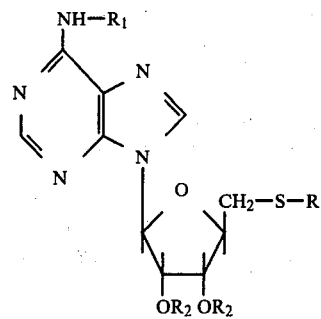

(Ib)

in which R, $R_1$, $R_2$ are as heretofore defined, provided that $R_1$ and $R_2$ are other than H or an isopropylidene chain, have been prepared by the Satom and Makino method (Satom, K., Makino, K. (1951) Nature 167, 238) by reacting the corresponding compounds of formula (Ia) with the required acyl chloride in anhydrous pyridene. The products are preferably recrystallised from a 1:1 chloroform/petroleum ether mixture.

The compounds of formula:

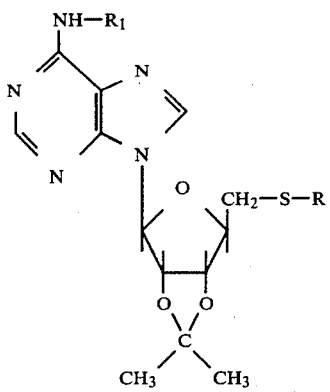

(Ic)

in which R and $R_1$ are as heretofore defined, are prepared by reacting the corresponding compounds of formula (I), in which $R_2$ is H, with acetone in the presence of $ZnCl_2$, again by the Satom and Makino method (referred to previously). The obtained products are purified preferably by crystallisation from a 1:1 chloroform/petroleum ether mixture. The compounds of formula:

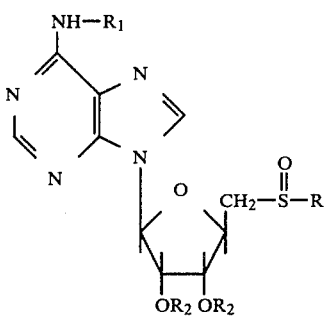

(Id)

in which R, $R_1$, $R_2$ are as heretofore defined, are prepared by oxidation of the corresponding thioethers, obtained by the methods heretofore indicated, by means of bromine or hydrogen peroxide in aqueous solution (Green Stein, J. P., Winitz, M. (1961)—Chemistry of the amino acids—John Wiley & Sons Inc. 2146). The products obtained are purified by recrystallisation from water.

Of all the products prepared, the one which has proved particularly interesting for the purposes of the present invention is 5'-deoxy-5'-methylthioadenosine (MTA) of formula

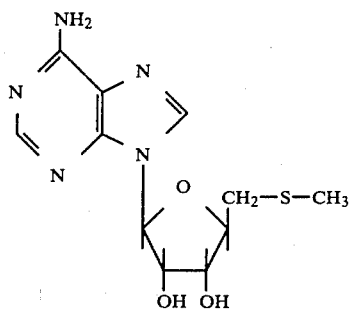

(II)

in which is a physiological compound already present in living organisms. A method has been found for preparing this product which is particularly simple and economical from an industrial viewpoint.

The new process consists essentially of carrying out hydrolysis of the S-adenosylmethionine (SAME) under strictly controlled critical conditions, which lead to practically total hydrolysis and complete crystallisation of the MTA

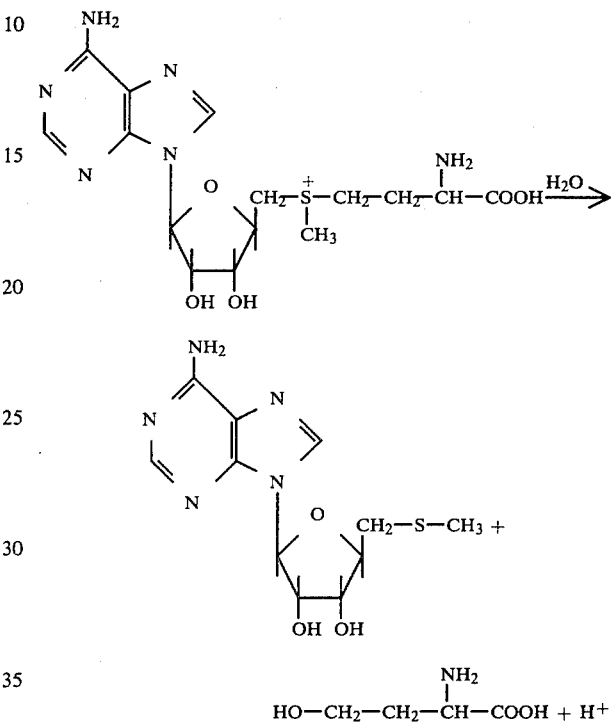

The controlled hydrolysis process can be applied to SAME prepared in any manner.

However, the method of preparation of the SAME solution is also an influencing factor in carrying out the new process in an economically convenient manner.

The following operational stages provide the most economical embodiment of the process:

(a) Normal bread yeast is enriched in SAME by treatment with methionine in accordance with the Schlenk method (Schlenk, F. (1965) Enzymologie 29, 283).

(b) The yeast cells suspended in water are lysised by treatment with ethyl or methyl acetate at ambient temperature (DT-OS P23 36401.4). By adjusting the pH to between 4 and 6 and filtering, an aqueous solution is obtained containing practically all the SAME present in the initial yeast (c) The solution is concentrated under vacuum at 35°–40° C. to about 1/10 of its initial volume (d) The concentrate is boiled under reflux for about 30 minutes and the pH adjusted to 7 with soda (e) The solution is left to stand at 0–5° C., and the precipitated MTA is collected practically completely and at good purity.

The stages c, d and e, which as stated are critically necessary for obtaining complete selective hydrolysis of SAME to MTA without formation of by-products, are new.

The preparation of some products used according to the present invention are described hereinafter.

EXAMPLE 1

Preparation of 5'-deoxy-5'-methylthioadenosine (MTA)

11 liters of ethyl acetate and 11 liters of water at ambient temperature are added to 90 kg of bread yeast which has been enriched in SAME by addying methionine until the SAME content is 6.88 g/kg.

After energetic stirring for 30 minutes, the pH is adjusted to 4.5 with dilute $H_2SO_4$, the mixture is filtered and the residue is washed with water to give 140 liters of solution with a SAME content of 4.40 g/l, equal to 99.5% of the SAME present in the initial material.

The lysate thus obtained is concentrated under vacuum (30 mm Hg; 35°–40° C.) to a volume of about 14 liters. The concentrated solution is boiled under reflux at normal pressure for 30 minutes. It is cooled to 20° C., the pH adjusted to 7 with 40% soda, and left overnight in a refrigeration cell (+3° C.). A white precipitate is formed which is filtered, dissolved in 10 liters of boiling distilled water and crystallised by cooling this solution.

410 g of crystalline MTA of high purity are obtained, equal to a yield of 90% with respect to the SAME subjected to hydrolysis.

The characteristics of the product obtained coincide with those of pure MTA obtained by other means.

EXAMPLE 2

Preparation of 5'-deoxy-5'-ethylthioadenosine 1 kg of adenosine is dissolved under a nitrogen atmosphere in 10 l of hexamethylphosphoramide, and 7.5 l of thionyl chloride are added under cooling.

The mixture is left to react at ambient temperature for 20 hours.

10 l of water are added, and the mixture neutralised with 2 N NaOH.

The 5'-deoxy-5'-chloroadenosine which thus forms is allowed to crystallise overnight at 3° C. It is filtered off. 0.950 kg of 5'-deoxy-5'-chloroadenosine are obtained (yield 89%).

0.950 kg of 5'-deoxy-5'-chloroadenosine are dissolved in 10 l of 2 N NaOH, and 200 ml of ethanethiol are added. The mixture is heated to 80° C. and left to react for 1 hour. It is neutralised with glacial acetic acid. The 5'-deoxy-5'-ethylthioadenosine which thus forms is allowed to precipitate overnight at 3° C. It is filtered off and recrystallised from water. 0.830 kg of product are obtained (yield 80% with respect to the preceding stage).

EXAMPLE 3

Preparation of other compounds of class Ia

The method as described in example 2 is carried out, but using propanethiol, butanethiol, isobutanethiol, pentanethiol, hexanethiol and benzylythiol respectively, in place of the ethanethiol.

EXAMPLE 4

Preparation of $N^6$,2',3'-triacetyl-5'-deoxy-5'-thioadenosine 1 kg of MTA is suspended in 10 l of anhydrous pyridine, and 3 l of acetic anhydride are added. The mixture is left to react for 4 hours. 20 l of water are added, and the mixture concentrated under vacuum to give an oily mass free from pyridine. This is dissolved in a hot 1:1 mixture of petroleum ether/chloroform (10 l) and left to crystallise. The product is recrystallised from a 1:1 petroleum ether/chloroform mixture. 1.140 kg of product are obtained (yield 80%).

EXAMPLE 5

Preparation of other compounds of class Ib

The method described in example 4 is carried out, but using other thioethers or propionic anhydride, butyric anhydride, benzoyl chloride or tosyl chloride instead of MTA.

EXAMPLE 6

Preparation of 5'-deoxy-2',3'-isopropylidene-5'-methylthioadenosine 1 kg of MTA are suspended in 25 l of anhydrous acetone, and 2.5 kg of molten $ZnCl_2$ are added. Reaction is carried out under reflux for 5 hours. The mixture is then concentrated under vacuum to ⅓ of its initial volume, and 7.5 kg of barium hydroxide octahydrate in aqueous suspension are added. Carbon dioxide is then bubbled through until neutral. The mixture is filtered and the residue washed with acetone. The filtrate is concentrated under vacuum to give a syrupy residue. It is taken up in a hot 1:1 chloroform/petroleum ether mixture (10 l), filtered and left to crystallise.

The product is recrystallised from 1:1 chloroform/petroleum ether, to give 0.795 kg of product (yield 70%).

EXAMPLE 7

Preparation of other compounds of class Ic

The methods as described in example 6 is carried out, but starting from the corresponding adenosine derivatives instead of MTA.

EXAMPLE 8

Preparation of MTA sulphoxide 1 kg of MTA are suspended in 10 l of water, and bromine is added under cooling.

The aqueous solution containing bromine is immediately decoloured by the oxidation of the MTA to sulphoxide.

Addition of bromine is continued until solution does not decolourise further.

The solution is decolourised by further addition of small quantities of MTA.

The aqueous solution is treated with Amberlite IRA 93 resin (registered trademark of Rohm and Haas for a weakly basic ion exchange resin with a polystyrene matrix) until the reaction of the bromide ions disappears.

The mixture is filtered and the residue washed with water.

The aqueous solution is concentrated to 10 l, treated with activated carbon (100 g) and lyophilised.

0.950 kg of product are obtained (yield 90%).

EXAMPLE 9

Preparation of other compounds of class Id

The method described in example 8 is followed, but starting from the corresponding adenosine derivatives instead of MTA.

As initially stated, it has been found that the compounds of formula I possess strong antiinflammatory activity, accompanied by analgesic and antipyretic action.

The antiinflammatory activity was demonstrated initially for some terms of the class by the test of experimental edema in the rat by carragen, by determining the percentage protection by the Winter method (J. Pharm. exper. Therap. 141, 369 1963). The values obtained are shown in Table 1.

TABLE 1

| Compound of formula (I) | Dose administered orally mg/kg | Percent protection calculated on edema development |
|---|---|---|
| n = 0 R = —CH$_2$, R$_1$ = R$_2$ = H | 37 | 50 |
| n = 0 R = —CH$_3$, R$_1$ = R$_2$ = H | 23 (a) | 50 |
| n = 0 R = —CH$_2$—C$_6$H$_5$, R$_1$ = R$_2$ = H | 47 | 10 |
| n = 0 R = —CH$_2$—CH(CH$_3$)$_2$ , R$_1$ = R$_2$ = H | 85 | 62 |
| n = 0 R = —(CH$_2$)$_6$—CH$_3$, R$_1$ = R$_2$ = H | 95 | 20 |
| n = 0 R = —(CH$_2$)$_{11}$—CH$_3$, R$_1$ = R$_2$ = H | 112 | 10 |
| n = 0 R = —(CH$_2$)$_4$—CH$_3$, R$_1$ = R$_2$ = H | 90 | 25 |
| n = 0 R = —CH$_2$—CH$_3$, R$_1$ = R$_2$ = H | 80 | 44 |
| n = 0 R = —(CH$_2$)$_2$—CH$_3$, R$_1$ = R$_2$ = H | 80 | 53 |
| n = 0 R = —CH(CH$_3$)$_2$ , R$_1$ = R$_2$ = H | 80 | 45 |
| n = 0 R = —(CH$_2$)$_3$—CH$_3$, R$_1$ = R$_2$ = H | 85 | 39 |
| n = 0 R = CH(CH$_3$)—CH$_2$—CH$_3$, R$_1$ = R$_2$ = H | 85 | 35 |
| n = 0 R = —(CH$_2$)$_7$—CH$_3$, R$_1$ = R$_2$ = H | 100 | 47 |
| n = 0 R = —(CH$_2$)$_9$—CH$_3$, R$_1$ = R$_2$ = H | 106 | 33 |
| n = 1 R = —CH$_3$, R$_1$ = R$_2$ = H | 156 | 50 |
| n = 1 R = —CH$_3$, R$_1$ = R$_2$ = H | 8.6 (a) | 50 |
| n = 0 R = —CH$_3$, R$_1$ = R$_2$ = —CO—CH$_3$ | 114 | 47 |
| n = 0 R = —CH$_3$, R$_1$ = R$_2$ = tosyl | 204 | 15 |
| n = 0 R = —CH$_3$, R$_1$ = R$_2$ = —CO—C$_6$H$_5$ | 164 | 10 |
| n = 0 R = —CH$_3$, R$_1$ = H, R$_2$—R$_1$ = isopropyl | 91 | 20 |
| Indomethacine | 9 | 50 |

(a) signifies that the product was administered intramuscularly.

As can be seen from this table, the ED$_{50}$ of the MTA is 37 mg/kg, and is thus the lowest of those of the compounds tested when administered orally.

In the same test, the ED$_{50}$ of indomethacine is 9 mg/kg. At these doses, there is the appearance of serious gastric lesions, whereas at the ED$_{50}$ doses the MTA gives rise to no secondary effect on the gastro-intestinal system. It should also be noted that the LD of indomethacine in the rat is 12 mg/kg (Martelli A. in Aspetti di farmacologia dell'infiammazione, page 73, published by Tamburini—Milan 1973), whereas the LD$_{50}$ of MTA in the rat is 200 mg/kg/oa.

The following therapeutical indices are therefore obtained:

| Indomethacine | TI = | 1.3 |
|---|---|---|
| MTA | TI = | >54.05 |

The compounds according to the invention were also subjected to a series of pharmacological tests for the purpose of confirming their antiinflammatory activity and for demonstrating their analgesic and antipyretic activity.

The results obtained in some of these tests with MTA are given hereinafter, this being a product which in all cases proved to be the most active when administered orally, and which is certainly the safest as it is a compound physiologically present in the organism, as already stated.

Again from the industrial production viewpoint, the method for producing MTA from SAME as discovered is by far the most simple and economical, and enables it to be marketed at a particularly low price.

As can be seen from the data of table 1, methylthioadenosine sulphoxide is particularly active when administered intramuscularly.

The greater activity of said compound on intramuscular administration was confirmed in all the tests carried out. Some significant data regarding MTA sulphoxide are also given, however it should be noted that all the compounds tested were in all cases shown to be active, although at different levels.

A—Antiinflammatory activity

The products were tested by pleuritis induced in the rat by carragen in accordance with the Velo method (Velo G. P., Dunn C. J. et al. (1973) J. Path. 111, 149).

MTA at a dose of 75 mg/kg by oral administration gave a protection of 42.4% calculated on the volume of the exudate, and 48.8% calculated on the total number of cells present in the exudate.

A comparable protection was obtained with 10 mg/kg of indomethacine, i.e. with a dose much closer to the LD$_{50}$. In the same test, the MTA sulphoxide gives a protection of 75.8% calculated on the volume of the exudate, and 76.4% calculated on the total number of cells present in the exudate when administered intramuscularly at a dose of 80 mg/kg.

B—Antiinflammatory Activity

In the granuloma test in the rat by cotton pellets (Winter C. A., Riseley, E. A. et al. (1963) J. Pharm. Exper. Ther. 141, 369), which is significant for chronic inflammation, the MTA gave a protection of 30% with an oral dose of 9 mg/kg, with a TI of 222.

C—The Analgesic Activity of the Products Was Tested by Two Tests Considered Very Significant In the hot plate test on the mouse according to Roberts (Roberts E. Simonsen D. G. (1966) Biochem. Pharmac. 15, 1875–) the MTA gives a protection of 50% with an oral dose of 37 mg/kg. An approximately equivalent protection of 58% is obtained with 100 mg/kg of amidopyrine administered orally.

In the same test MTA sulphoxide gives a protection of 50% at a dose of 20 mg/kg when administered intramuscularly, and at a dose of 100 mg/kg when administered orally.

In the stretching test by phenylquinone (Siegmund E., Cadmus R., GO-LU (1957) Proc. Soc. Exp. Biol. Med. 95, 729), the MTA gives a protection of 51% at an oral dose of 37 mg/kg.

In the same test, MTA sulphoxide has an $ED_{50}$ of 10 mg/kg when administered intramuscularly.

D—Antipyretic Activity

This was measured for the new products by means of fever induced in the rat by beer yeast (Winder C. V. et al (1961) J. Pharmacol. Exp. Ther. 133, 117).

The antipyretic effect evaluated one hour after oral administration of MTA at a dose of 300 mg/kg gave a temperature reduction of 4.59% with respect to the controls, which were treated only with yeast. This percentage corresponded to a temperature lowering from 38.8° C. to 37.4° C.

By comparison, amidopyrine administered orally at a dose of 200 mg/kg produced a temperature reduction of 4.69%, and intramuscular administration of MTA at a dose of 80 mg/kg gave a temperature reduction of 2.35%.

E—Platelet antiaggregation activity

The compounds of the invention have also been evaluated with respect to their possible platelet antiaggregation capacity.

Platelet aggregation is known to be a complex phenomenon which can be divided into a primary stage due to the direct action of a stimulus (for example adenosine diphosphate, i.e. ADP, or epinephrin) and a secondary stage due to the aggregation induced by the ADP released by the platelets. In this respect, when the platelets come into contact with the subendothelial collagen, the collagen initiates an entire series of reactions which lead to the release of ADP by the platelets. It is this ADP which causes the second wave of platelet aggregation.

The following tests were carried out in order to evaluate the antiaggregation effect of the new compounds:

(1) "in vitro" tests on platelet aggregation induced by ADP and collagen, in the presence of the new products;

(2) "in vitro" tests on platelet aggregation induced by arachidonic acid (AA);

(3) "in vivo" tests on platelet aggregation induced by ADP and collagen in persons treated with the new products.

In this case the most significant results were again obtained with MTA, because of which the results obtained using this product are given as indicative of the behaviour of the entire class.

(1) "In vitro" tests.

Blood was withdrawn without stasis, and an anticoagulant (3.8% sodium citrate) was added to give a blood:citrate ratio of 9:1. Plasma rich in platelets and plasma poor in platelets were obtained by centrifuging at ambient temperature.

The platelet aggregation was estimated using the Born & Cross method (G. V. R. Born and M. J. Cross, J. Physiol., Lond. 168, 178, 1963) on the plasma fraction rich in platelets.

The aggregating agents were used in the following concentrations: ADP (Sigma) 1 $\mu$M; collagen (Horn) 5 $\mu$g/ml; arachidonic acid $4 \times 10^{-4}$ M.

Adenosine at a concentration of $1 \times 10^{-5}$ M was used as the antiaggregation activity reference substance.

The results obtained with ADP are shown on the graphs of FIG. 1, in which the abscissa indicates the time in minutes and the ordinate the percentage aggregation.

Curve 1 relates to the controls, curve 2 to the samples treated with $1 \times 10^{-5}$ Madenosine, and curve 3 to the samples treated with $5 \times 10^{-4}$ M MTA.

From the curve pattern it is apparent that MTA strongly reduces primary platelet aggregation due to ADP, and as a consequence inhibits the 2nd aggregation wave.

The same tests carried out with collagen gave negative results, i.e. MTA showed no inhibiting power towards platelet aggregation induced by collagen which was worthy of note.

Figure 2:
Figure 3:

(2) FIG. 2 shows the effects of various MTA concentrations on platelet aggregation induced by AA at a concentration of $4 \times 10^{-4}$ M. Curve 1 relates to the controls, curve 2 to MTA at a concentration of $2.5 \times 10^{-4}$ M, curve 3 to MTA at a concentration of $5 \times 10^{-4}$ M, and curve 4 to MTA at a concentration of $10^{-3}$ M. As is apparent, the platelet aggregation inhibiting effect of the MTA is proportional to its concentration. The capacity of MTA to increase the inhibiting effect of prostacyclin ($PGI_2$) in aggregation induced by AA was also investigated. In FIG. 3, curve 1 relates to the controls, curve 2 to MTA at a concentration of $5 \times 10^{-4}$ M, curve 3 to $PGI_2$ at a concentration of $5 \times 10^{-9}$ M, and curve 4 to a mixture consisting of $5 \times 10^{-4}$ M MTA and $5 \times 10^{-9}$ M $PGI_2$. It is apparent from FIG. 3 that when used in mixture there is a strong increase in the antiaggregation action at concentrations which are in themselves ineffective.

(3) "In vivo" tests

Three apparently healthy volunteer subjects aged 35, 42 and 48 years respectively, and who had not taken any drug for at least 15 days, were submitted to aggregation tests before and after consuming the new products at a dose of 100 mg every 8 hours for 3 days, these tests then being evaluated. The blood sample for the determination of the platelet aggregation was taken 2 hours before consuming the last dose of product under test.

Figure 4:
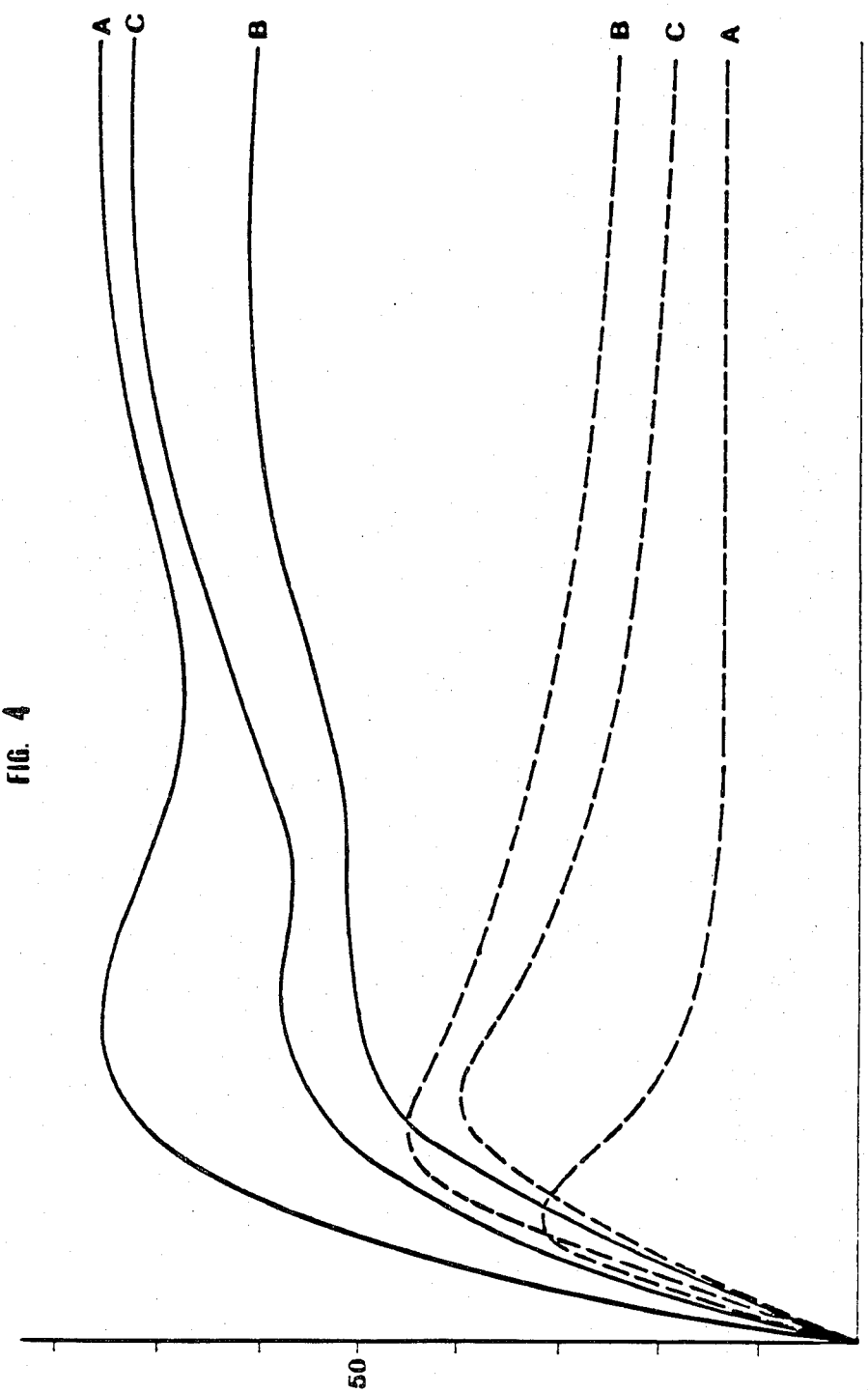

FIG. 4 shows the results obtained with MTA.

More precisely, the full-line curves relate to the values obtained with blood samples from untreated patients, whereas the dashed-line curves relate to the values obtained for the same patients treated with MTA.

It is apparent that MTA strongly inhibits platelet aggregation induced by ADP (1 $\mu$M) "in vivo".

The same tests repeated on adding 5 $\mu$g/ml of collagen to the blood demonstrated that MTA is not effective in inhibiting platelet aggregation induced by collagen, but only lengthens the latency time of the phenomenon.

The fact that MTA (and in a more or less comparable manner the other products of the same class) strongly inhibits platelet aggregation induced by ADP, whereas it has practically no effect on aggregation induced by collagen, indicates that MTA inhibits the 1st aggregation wave, whereas it has a negligible direct effect on the 2nd aggregation wave.

Its use in association with other known antiaggregation drugs which are generally active towards the 2nd wave whereas are only poorly effective towards the 1st wave is therefore particularly interesting.

The demonstrated activity suggests the use of MTA (and of the other compounds of the series, even if less effective) not only as a platelet antiaggregation drug, but also as an anti-thrombotic and antiatherosclerotic drug, in that, besides being the basis of thrombogenesis mechanisms, the altered relationship between platelets and vasal walls also plays a primary role in atherosclerotic illness.

F—Sleep Inducing Activity

The Morris test was used (Morris R. W. (1966) Arch. int. Pharmacodyn 161, No. 2, 380)

In this test, the MTA increased by 87% the duration of the sleep induced by pentobarbital in the mouse, at an intramuscular dose of 20 mg/kg.

G—Acute Toxicity

The compounds of the present invention are practically free from acute toxicity when administered orally. They are practically free from toxicity at therapeutic doses for any method of administration.

The following values are obtained for MTA and MTA sulphoxide:

|  |  |  |
|---|---|---|
| MTA - DL$_{50}$ in the mouse orally | >2000 | mg/kg |
| intravenously | 360 | mg/kg |
| MTA sulphoxide - DL$_{50}$ in the mouse orally | >2000 | mg/kg |
| intravenously | 400 | mg/kg |

The adenosine derivatives of formula (I) can be administered, diluted with suitable pharmacologically acceptable excipients, in any therapeutically useful form, orally, parenterally or by venous or rectal means. They can also be used in products for external use by topical application.

Some examples of typical pharmaceutical compositions with MTA are given hereinafter by way of example:

| 100 mg capsules | | |
|---|---|---|
| MTA | 100.2 | mg |
| Mannitol | 195.0 | mg |
| Magnesium stearate | 15.0 | mg |
|  | 300.2 | mg |
| 50 mg capsules | | |
| MTA | 50.1 | mg |
| Mannitol | 100.0 | mg |
| Magnesium stearate | 3.0 | mg |
|  | 153.1 | mg |
| 100 mg tablets | | |
| MTA | 100.2 | mg |
| Starch | 100.0 | mg |
| Magnesium stearate | 15.0 | mg |
| Lactose | 85.0 | mg |
|  | 300.2 | mg |
| 50 mg tablets | | |
| MTA | 50.1 | mg |
| Starch | 120.0 | mg |
| Magnesium stearate | 15.0 | mg |
| Lactose | 115.0 | mg |
|  | 300.1 | mg |
| 100 mg suppositories | | |
| MTA | 100.2 | mg |
| Suppository mass | 1,700.0 | mg |
|  | 1,800.2 | mg |
| 50 mg suppositories | | |
| MTA | 50.1 | mg |
| Suppository mass | 1,450.0 | mg |
|  | 1,500.1 | mg |
| 50 mg injectable phial | | |
| MTA.HCl (56.15 mg basically equivalent) | 50 | mg |
| Lidocain HCl | 25 | mg |
| Water to make up to | 3 | ml |
| 25 mg injectable phial | | |
| MTA.HCl (28.07 mg basically equivalent) | 25 | mg |
| Lidocain HCl | 20 | mg |
| Water to make up to | 2 | ml |
| 100 mg oral dose | | |
| MTA.HCl (112.3 mg basically equivalent) | 100 | mg |
| Citrus flavouring | 0.025 | mg |
| Sugar | 1 | g |
| Antifermenting agent | 50 | mg |
| Water to make up to | 5 | ml |
| 50 mg oral dose | | |
| MTA.HCl (56.15 mg basically equivalent) | 50 | mg |
| Citrus flavouring | 0.015 | mg |
| Sugar | 0.5 | g |
| Antifermenting agent | 30 | mg |
| Water to make up to | 5 | ml |
| 100 g ointment | | |
| MTA | 5 | g |
| Base for water soluble ointment, to make up to | 100 | g |
| Antioxidant | 0.1 | g |

We claim:

1. A process for preparing 5'-deoxy-5'-methylthioadenosine, wherein S-adenosyl-methionine, in concentrated aqueous solution, is hydrolysed by heating under reflux, and the 5'-deoxy-5'-methylthioadenosine formed is separated by cooling after neutralising the reaction mixture.

2. A process as claimed in claim 1, wherein the aqueous solution of S-adenosyl-methionine is concentrated by heating under vacuum to 35°–40° C.

3. A process as claimed in claim 1, wherein the 5'-deoxy-5'-methylthioadenosine formed is precipitated by cooling to 0°–5° C.

* * * * *